US00PP29726P2

(12) United States Plant Patent
Olesen

(10) Patent No.: US PP29,726 P2
(45) Date of Patent: Oct. 9, 2018

(54) MINIATURE ROSE PLANT NAMED 'POULPAH083'

(50) Latin Name: ***Rosa* hybrid**
Varietal Denomination: Poulpah083

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensboro (DK)

( * ) Notice: Subject to any disclaimer, the term of this patent is extended or adjusted under 35 U.S.C. 154(b) by 0 days.

(21) Appl. No.: 15/731,981

(22) Filed: Sep. 5, 2017

(51) Int. Cl.
*A01H 5/02* (2018.01)

(52) U.S. Cl.
USPC ..... Plt./121

(58) Field of Classification Search
USPC ..... Plt./121
See application file for complete search history.

*Primary Examiner* — Annette H Para

(57) ABSTRACT

A new garden rose plant of the Miniature class which has abundant, Pink flowers and attractive foliage. This new and distinct variety has shown to be uniform and stable in the resulting generations from asexual propagation.

3 Drawing Sheets

Botanical designation: *Rosa* hybrid.
Variety denomination: 'Poulpah083'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpah083', originated as a single seedling from the stated cross.

The new variety may be distinguished from its male pollen parent and female seed parent primarily by the following characteristics. The male pollen parent plant has dark red flowers while the new variety has pink flowers. The female seed parent plant has orange red flowers while the new variety has pink flowers.

The objective of the hybridization of this rose variety was to create a new and distinct variety with unique qualities, such as:

1. Uniform and abundant Pink flowers;
2. Vigorous, but compact growth when propagated on its own roots;
3. Exceptional disease resistance.

This combination of qualities is not present in previously available commercial cultivars of this type, known to the inventor, and distinguish 'Poulpah083' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpah083' was selected in the spring of 2011 by the inventor as a single plant from the progeny of the aforementioned hybridization.

Asexual reproduction of 'Poulpah083' by rooted cuttings was first done by Mogens N. Olesen in the nursery in Fredensborg, Denmark in July, 2011. This initial and other subsequent asexual propagations conducted in controlled environments have demonstrated that the characteristics of 'Poulpah083' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah083'.

Specifically illustrated in FIG. 1 of the drawings are flower buds, petals and sepals detached.

DETAILED DESCRIPTION OF THE VARIETY

Figure 1:
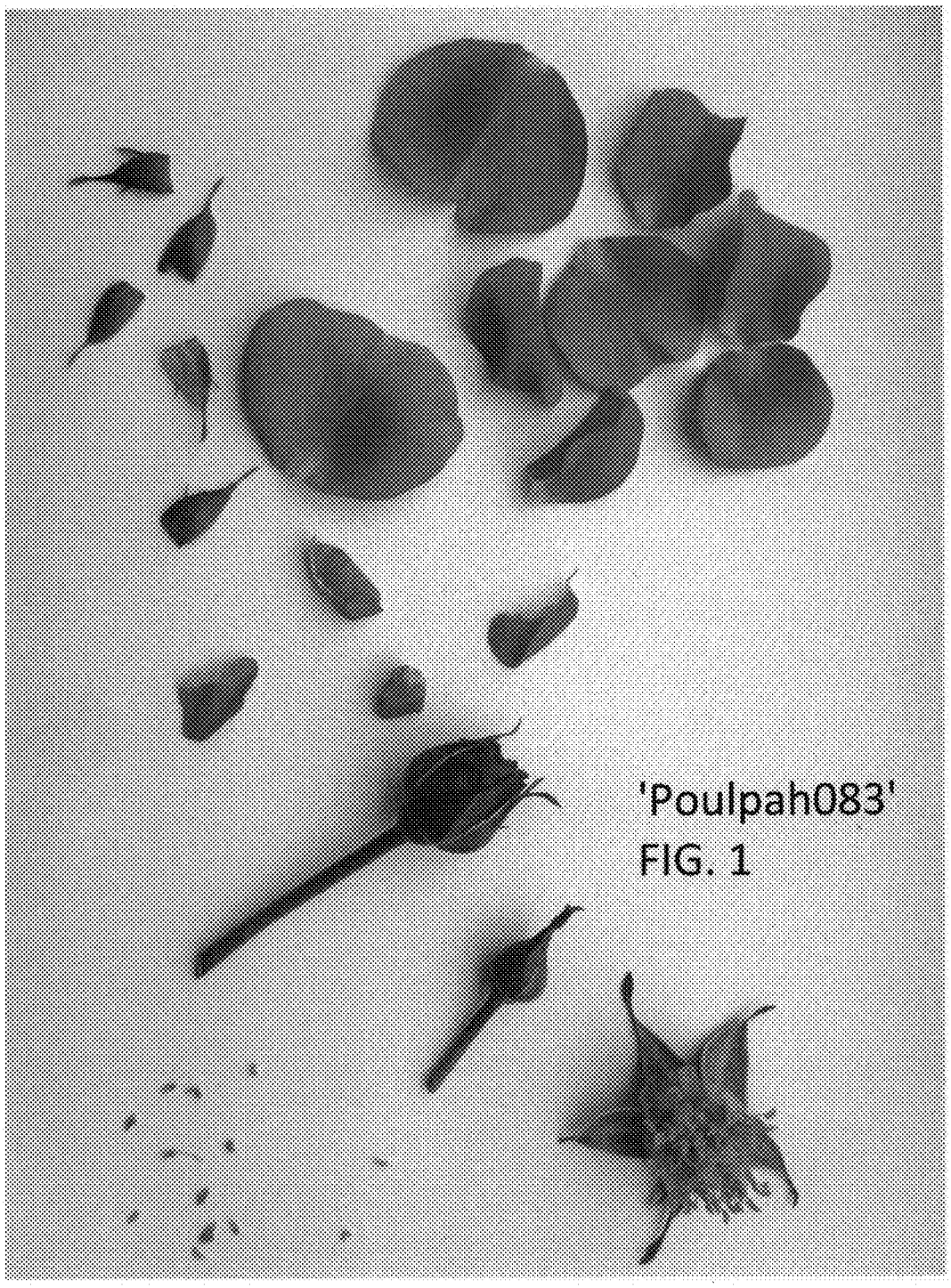
Figure 2:
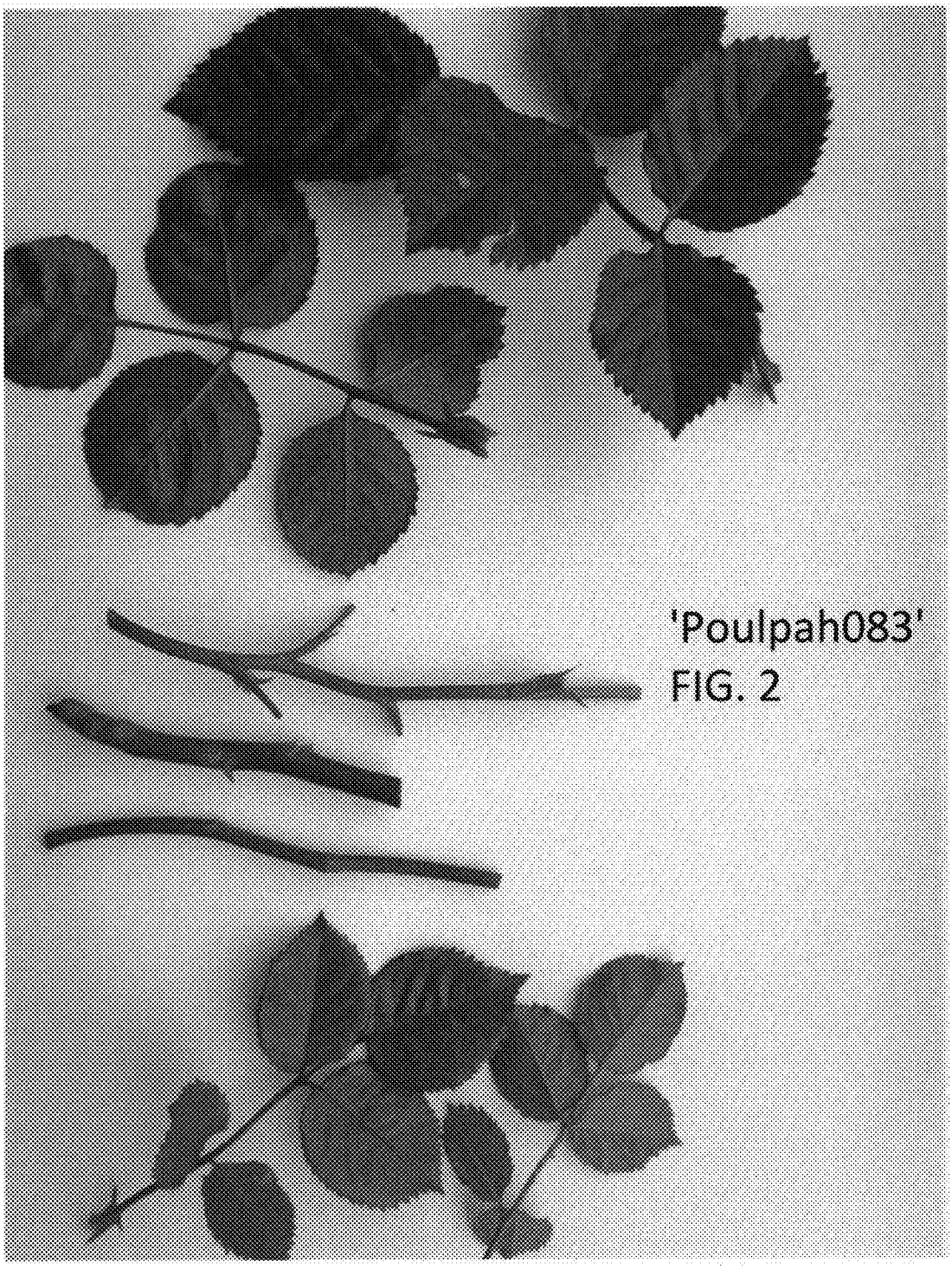
FIG. 2 shows leaves and bare stems.
Figure 3:
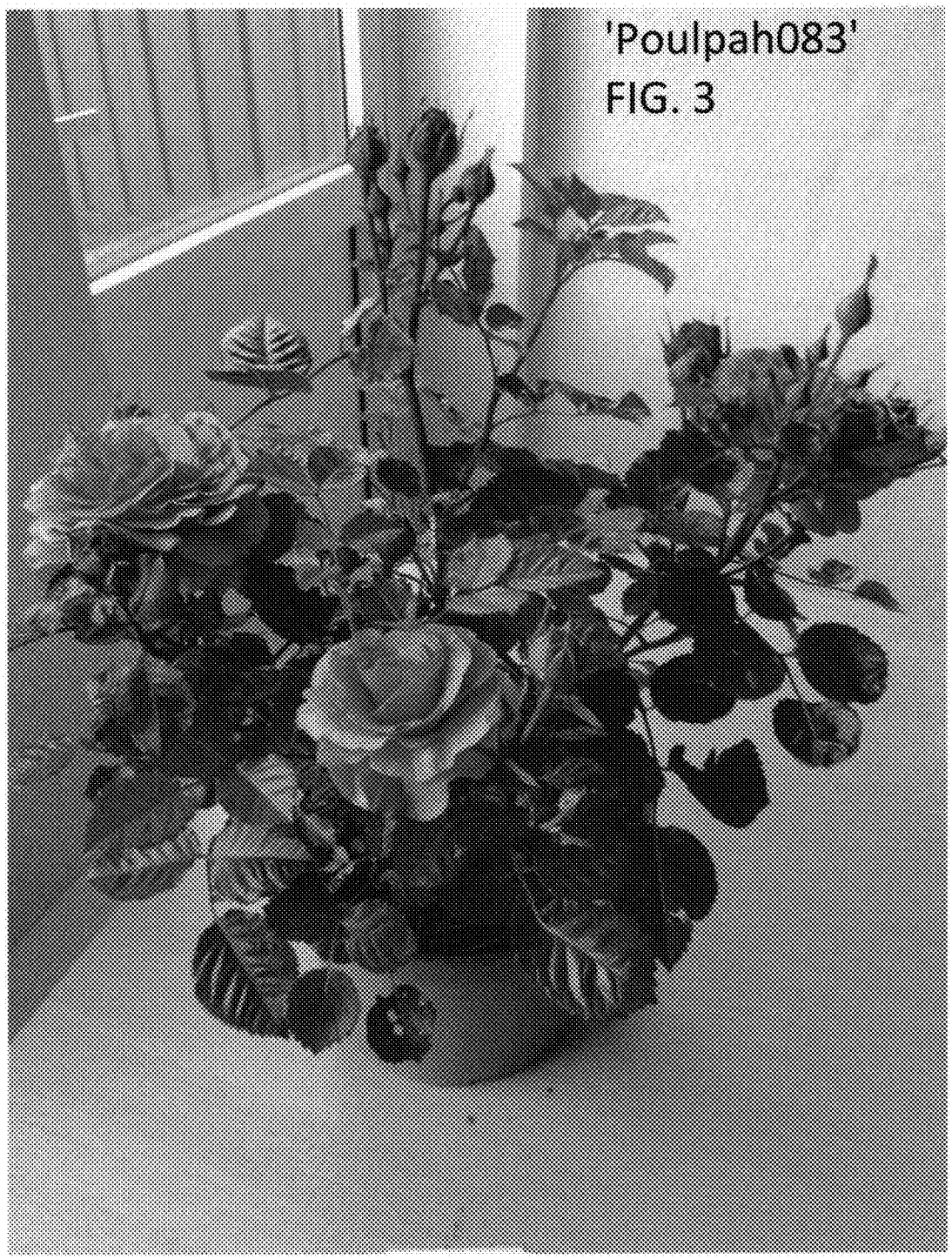
FIG. 3 shows the entire flowering plant. Plants shown are 1 year old.

The following is a description of 'Poulpah083', as observed in its growth in 24 cm containers, in Odense Denmark. Observed plants are 1 year in age, and were grown on their own roots. Color references are made using The Royal Horticultural Society (London, England) Colour Chart, 2001, except where common terms of color are used.

For a comparison, several physical characteristics of the rose variety 'Poulpah082', are compared to 'Poulpah083' in Chart 1.

CHART 1

| | 'Poulpah083' | 'Poulpah082' |
|---|---|---|
| Petal Count | 65 | 35 |
| Flower Diameter | 90 mm | 90 mm |
| General Tonality of Flower Color | Red Group 55A | Red-Purple Group 58C and Red-Purple Group 62B |

FLOWER AND FLOWER BUD

Blooming habit: Continuous.

Flower bud:

*Size*.—Upon opening, 22 mm in length from base of receptacle to end of bud. Bud diameter is 12 mm.

*Bud form*.—Ovoid.

*Bud color*.—As sepals divide petals are Red- Purple Group 60A.

*Sepal inner surface*.—Color: Yellow-Green Group 147C. Surface: Moderately pubescent.

*Sepal outer surface*.—Color: Yellow-Green Group 146A with intonations of Red-Purple Group 59A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—24 mm long, 10 mm wide.

*Receptacle*.—Texture: Smooth. Size: 3 mm in height, 9 mm wide. Color: Yellow-Green Group 144A with intonations of Red-Purple Group 59A. Shape: Broad funnel.

*Pedicel*.—Surface: Smooth. Length: 20 to 50 mm. Diameter: 3 mm on average. Color: Yellow-Green Group 146C with intonations of Red-Purple Group 59A. Strength: Strong.

*Peduncle*.—Length: 3 to 20 cm. Diameter: About 3 mm. Color: Yellow-Green Group 146B with intonations of Red-Purple Group 59A. Texture: Smooth.

Flower bud development: Flower buds are borne in clusters of 5 to 12 flower buds per stem. Development as corymb.

Flower bloom:

*Fragrance*.—Light floral.

*Duration*.—The blooms have a duration on the plant of approximately 10 days. Petals do not fall cleanly away from plant after flowers have fully matured.

*Size*.—Flower diameter is 90 mm when open. Flower depth is 30 mm.

*Flower shape*.—Rosette, very double flower with many slightly overlapping petals of different sizes.

*Shape of flower, side view*.—The upper portion is flattened convex. The lower portion is a flattened convex.

Petalage: Under normal conditions, flowers have about 65 petals.

General tonality of flower: Open flowers are Red Group 55A.

Petal color:

*Upon opening, and after opening, inner and outer petals*.—Upper surface: Red Group 55A. Lower surface: Red Group 54A.

*Basal petal spots*.—Upper surface: Yellow Group 12A. Lower surface: Yellow Group 12B.

Petals:

*Petal reflex*.—Somewhat reflexed.

*Margin*.—Entire and uniform. Moderate undulations on some petals.

*Shape*.—Broad and elliptic. Apex shape: Rounded. Base shape: Obtuse.

*Size*.—60 mm (l)×30 mm (w).

*Texture*.—Smooth.

*Thickness*.—Average.

Petaloids:

*Size*.—25 mm (l) by 15 mm (w).

*Quantity*.—About 10.

*Shape*.—Elliptical with an acute base and rounded apes.

*Color*.—Upper surface is Red Group 55A with a basal petaloid spot of Yellow Group 12A. The lower surface is Red Group 54A with a basal spot of Yellow Group 12B.

Reproductive flower parts:

*Pollen*.—None observed.

*Anthers*.—Size: 3 mm in length. Color: Yellow-Orange Group 23A. Quantity: 120 on average.

*Filaments*.—Color: Yellow Group 11B. Length: 7 mm.

*Pistils*.—Length: 5 mm. Quantity: 70 on average.

*Stigmas*.—Color: Yellow Group 12B.

*Styles*.—Color: Greyed-Yellow Group 1D.

*Location of stigmas*.—Inferior in location relative to the length of the filaments and the height of the anthers.

*Hips*.—None Observed.

PLANT

Plant growth: Upright, bushy. Plants are 40 cm in height, and 35 cm wide.

Stems:

*Color of juvenile growth*.—Yellow-Green Group 146B.

*Color of mature growth*.—Yellow-Green Group 148A.

*Length*.—Canes are about 30 cm from the base of the plant to the flowering portion.

*Diameter*.—About 6 mm.

*Internodes*.—On mature canes about 35 mm between nodes.

*Surface texture*.—Young wood: Smooth. Older wood: Smooth.

Long prickles: None observed.

Plant foliage:

*Compound leaf*.—About 120 to 150 mm (l) and 80 to 120 mm (w).

*Quantity*.—3 leaves per 10 cm of stem on average.

*Leaf bearing angle to the stem*.—45 degrees.

*Color of juvenile foliage*.—Upper side: Yellow-Green Group 144A with intonations of Greyed-Red Group 183C. Lower side: Yellow-Green Group 146C.

*Color of mature foliage*.—Upper side: Yellow-Green Group 147A. Lower side: Yellow-Green Group 147B.

Plant leaves and leaflets:

*Stipules*.—Size: 11 mm long, 4 mm wide. Quantity: 2 per compound leaf. Shape: Linear, slightly broad based with outward extending apices. Margins: Finely serrated. Color: Yellow-Green Group 147A with intonations of Greyed-Red Group 178A.

*Petiole*.—Length: 30 mm. Diameter: 2 mm. Upper surface color: Yellow-Green Group 147A with intonations of Greyed-Red Group 178A. Lower surface color: Yellow-Green Group 146A.

*Rachis*.—Length: 20 to 35 mm. Upper surface color: Yellow-Green Group 147A. Lower surface color: Yellow-Green Group 146A.

*Leaflet*.—Quantity: Normally 5 leaflets. Margins: Serrated. Size: Terminal leaflets are about 35 to 70 mm long, 30 to 55 mm wide. Shape: Generally ovate. Base: Rounded. Apex: Acuminate. Texture: Rugose.

Thickness: Average. Arrangement: Odd pinnate. Venation: Reticulate. Glossiness: Very glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah083', substantially as illustrated and described herein, due to its abundant pink flowers, disease resistance, and extended period of bloom.

* * * * *

'Poulpah083'

'Poulpah083'

'Poulpah083'